United States Patent [19]
Sheikhnejad

[11] Patent Number: 5,874,416
[45] Date of Patent: Feb. 23, 1999

[54] RAS ANTISENSE INHIBITION

[76] Inventor: Gholamreza Sheikhnejad, 2224 Independence Boulevard, Ann Arbor, Mich. 48104

[21] Appl. No.: 965,868

[22] Filed: Nov. 7, 1997

[51] Int. Cl.[6] .......................... A61K 48/00; C07H 21/04; C12Q 1/68
[52] U.S. Cl. ................................ 514/44; 435/6; 435/91.1; 435/172.3; 435/325; 435/366; 435/375; 536/23.1; 536/24.31; 536/24.5
[58] Field of Search ............................ 435/6, 91.1, 172.3, 435/320.1, 366, 325, 375; 536/23.1, 24.31, 24.5; 514/44

[56] References Cited

FOREIGN PATENT DOCUMENTS

WO 94/29461  12/1994  WIPO ............................. C12N 15/63

OTHER PUBLICATIONS

Rachal et al. In Vitro DNA Cytosine Methylation of cis–Regulatory Elements Modulates c–Ha–ras Promoter Activity In Vivo. Nucleic Acids Res 17 (13), 5135–5147 (1989).

Bennett et al., Parmacology of Antisense Therapeutic Agents: Cancer and Inflammation, in Antisense Therapeutics, pp. 13–46, (Shudir Agrawal, ed. 1996).

Gewirtz et al., Facilitating oligonucleotide delivery: Helping antisense deleiver on its promise, PNAS 93, 3161–63 (1996).

Primary Examiner—John L. LeGuyader
Assistant Examiner—Mark L. Shibuya
Attorney, Agent, or Firm—Harness, Dickey & Pierce, P.L.C.

[57] ABSTRACT

A single stranded oligonucleotide complementary to a specific region of a gene promoter, methylated at carbon 5 of all cytosine residues in cytosine-guanine (CG) dinucleotides, is provided. The modified oligonucleotide provides DNA methyltransferase (MTase) enzyme with a hemimethylated substrate so that DNA MTase can methylate complementary CG sites using methylated oligonucleotides as the template. Such methylation prevents translation of the gene. An oligonucleotide complementary to the sense strand of c-Ha-ras promoter having a methyl group on all cytosine residues of its 6 CpG sites was specifically effective in inhibiting breast tumor cell proliferation and tumorigenicity.

12 Claims, 6 Drawing Sheets

RAS ANTISENSE INHIBITION

FIELD OF THE INVENTION

Compositions and methods for inhibiting the activity of specific genes are provided and in particular, modified oligodeoxyribonucleotides and methods of using same are provided which prevent transcription of certain gene sequences.

BACKGROUND OF THE INVENTION

Oncogenes have become the central concept in understanding cancer biology and may provide valuable targets for therapeutic drugs. One gene which has captured the attention of many scientists is the human proto-oncogene, c-Ha-ras. This gene acts as a central dispatcher, relaying chemical signals into cells and controlling cell division. Ras gene alteration may cause the gene to stay in the "on" position. The ras oncogene is believed to underlie up to 30% of cancer, including colon cancer, lung cancer, bladder and mammary carcinoma. Bos, J. L., *Cancer Res.* 49:4682–4689 (1989). The ras oncogene has therefore become a target for therapeutic drugs.

All oncogenes and their products operate inside the cell. This makes protein-based drugs ineffective since their specificity involves ligand-receptor recognition. However, antisense oligodeoxyribonucleotides (oligonucleotides) are capable of easily entering cells and they can specifically target oncogenes. Wickstrom, E. (ed). *Prospects for antisense nucleic acid therapy of cancer and Aids.* New York: Wiley-Liss, Inc. 1991; Murray, J. A. H. (ed). *Antisense RNA and DNA New York*: Wiley-Liss, Inc. 1992. Antisense drugs are modified synthetic oligonucleotides that work by interfering with ribosomal translation of the target mRNA. The antisense drugs developed thus far destroy the targeted mRNA by binding to it and triggering ribonuclease H (RNase H) degradation of mRNA. The antisense compounds in clinical trials are all approximately from 17 to 25 nucleotides long. Oligonucleotides have a half-life of about 20 minutes and they are therefore rapidly degraded in most cells. Fisher, T. L. et al., *Nucleic Acids Res.* 21:3857–3865 (1993). To increase the stability of oligonucleotides, they are often chemically modified, e.g., they are protected by a sulfur replacing one of the phosphate oxygens in the backbone (phosphorothioate). Milligan, J. F. et al., *J. Med. Chem.* 36:1923–1937 (1993); Wagner, R. W. et al., *Science* 260:1510–1513 (1993). However this modification can only slow the degradation of antisense and therefore large dosages of antisense drug are required to be effective. An additional problem with antisense drugs has been their nonspecific activities. Yet, despite these problems, many antisense drugs are in phase I, II and III of clinical trials.

There are several reports showing that oligonucleotides complementary to various sites of ras mRNA can inhibit synthesis of ras protein (p21) which decrease cell proliferation rate in cell culture. U.S. Pat. No. 5,576,208 (Monia et al.); U.S. Pat. No. 5,582,986 (Monia et al.); Daska, Y. et al., *Oncogene Res.* 5:267–275 (1990); Brown, D. et al., *Oncogene Res.* 4:243–252 (1989); Saison-Behmoaras, T. et al., *EMBO J.* 10:1111–1116 (1991). Oligonucleotides complementary to the 5' flanking region of the c-Ha-ras RNA transcript has shown to inhibit tumor growth in nude mice for up to 14 days. Gray, G. D. et al., *Cancer Res.* 53:577–580 (1993). It was recently reported that an antisense oligonucleotide directed to a point mutation (G>C) in codon 12 of the c-Ha-ras mRNA inhibited cell proliferation as well as tumor growth in nude mice when it was injected subcutaneously. U.S. Pat. No. 5,576,208 (Monia et al.); U.S. Pat. No. 5,582,986 (Monia et al.); Schwab, G. et al., *Proc. Natl. Acad. Sci. USA* 91:10460–10464 (1994). At the American Society of Clinical Oncology meeting in May 1997, researchers reported that antisense drugs shrank ovarian tumors in small clinical trials. Roush, et al. *Science* 276:1192–1194 (1997). At the same meeting it was reported that an oligonucleotide which blocks replication of cytomegalovirus that destroys the retinas of many AIDs patients, is already in phase III clinical trials.

Despite the optimism surrounding these studies, there are a number of serious problems with the use of antisense drugs such as difficulty in getting a sufficient amount of antisense into the cell, non-sequence-specific effects, toxicity due to the large amount of sulfur containing phosphothioates oligonucleotides and their inability to get into their target cells, and high cost due to continuous delivery of large doses. It would thus be desirable to provide a composition which overcomes these difficulties.

SUMMARY OF THE INVENTION

An antisense composition is provided which inhibits tumor cell proliferation and tumorigenicity. In one embodiment, a single stranded oligonucleotide complementary to a specific region of a gene promoter is provided, which, when bound to the gene promoter, is capable of preventing transcription of the gene sequence. In another embodiment, an antisense oligonucleotide which is methylated is provided. In an alternative embodiment, methylated oligonucleotides complementary to specific gene promoter sequences are provided. In yet another embodiment, a single stranded oligonucleotide complementary to a specific region of gene promoter, methylated at carbon 5 of all cytosine residues in cytosine-guanine (CG) dinucleotides, is provided. The methylated oligonucleotides of the present invention provide an hemimethylated substrate for the DNA methyltransferase (MTase) enzyme. DNA MTase may then methylate complementary CG sites using methylated oligonucleotides as the template wherein such methylation prevents transcription of the gene (provided the gene is regulated via DNA methylation).

In a preferred embodiment of the present invention, a 26 mer oligonucleotide (RZ1X; SEQ ID NO: 1) is provided with a methyl group at the 5 position of all cytosine residues of its 6 CpG sites. RZ1X is complementary to the sense strand of c-Ha-ras promoter, upstream of TATA box between bases 485 and 511. RZ1X is able to down regulate transcription of the c-Ha-ras oncogene and is effective in inhibiting tumor cell proliferation and tumorigenicity, without effecting normal cells.

The promoter-specific methylated oligonucleotides of the present invention have many advantages over conventional antisense compositions. By way of illustration and in no way limiting the scope of the invention, it is believed that the promoter-specific methylated oligonucleotides of the present invention inhibit gene activity at the transcriptional level, therefore cells can not recycle their mRNA as quickly (if at all) to abolish the inhibitory effect of oligonucleotides. There is therefore no need for continuous delivery of large amounts of chemically-modified antisense, a major set back in current antisense therapy. Moreover, methylation is a naturally occurring modification in DNA, and it is therefore less likely to cause undesirable side effects.

Additional objects, advantages, and features of the present invention will become apparent from the following description and appended claims, taken in conjunction with the accompanying drawings.

BRIEF DESCRIPTION OF THE DRAWINGS

The various advantages of the present invention will become apparent to one skilled in the art by reading the following specification and subjoined claims and by referencing the following drawings in which:

FIG. 6 is a Northern blot of total RNA extracted from control and treated MCF-7 cells;

DETAILED DESCRIPTION OF THE PREFERRED EMBODIMENTS

Figure 1:
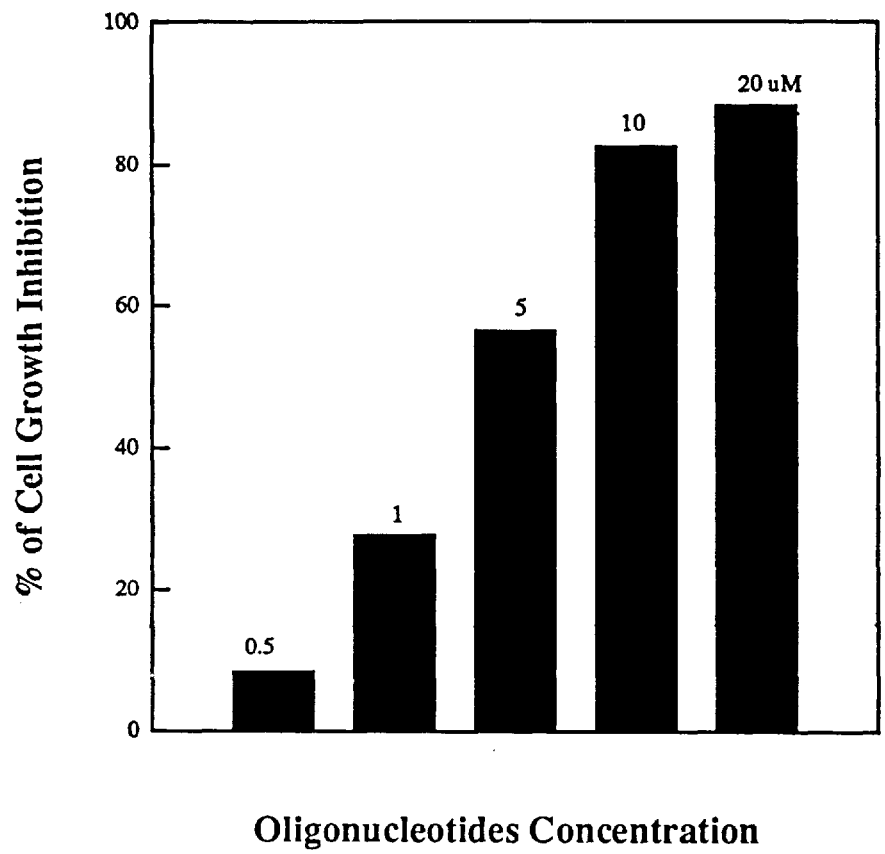
FIG. 1 is a graph showing the effect of various concentration of anti-ras oligonucleotides on MCF-7 cell growth.

The present invention provides oligonucleotides complementary to specific gene promoter sequences which inhibit transcription of the gene sequence. In particular, a single stranded oligonucleotide complementary to a specific region of gene promoter, methylated at carbon 5 of all cytosine residues in cytosine-guanine (CG) dinucleotides, is provided. The oligonucleotides of the present invention comprise from about 10 to about 50 nucleotides, wherein about 15 to about 35 nucleotides is preferred. In the methylated oligonucleotides, at least one cytosine (C) of a CG base pair contains a methyl group at the 5 position of the cytosine nucleotide. The methylated oligonucleotides of the present invention thus provide an hemimethylated substrate for the DNA methyltransferase (MTase) enzyme so that DNA MTase may methylate complementary CG sites using methylated oligonucleotides as the template, wherein such methylation prevents transcription (and hence translation) of the gene.

In one embodiment, a 26 mer oligonucleotide (RZ1X; SEQ ID NO: 1) is provided with a methyl group on all cytosine residues of its 6 CpG sites. RZ1X is complementary to the sense strand of c-Ha-ras promoter, upstream of TATA box between bases 485 and 511. RZ1X is able to down regulate transcription of the c-Ha-ras oncogene and is effective in inhibiting tumor cell proliferation and tumorigenicity, without effecting growth of normal cells.

One of the known mechanisms for the regulation of gene activity is methylation of cytosine residues in DNA. 5-methylcytosine (5-MeC) is the only naturally occurring modified base detected in DNA. Ehrlick, M. et al., *Science* 212:1350–1357 (1981). Although all genes are not regulated by methylation, hypomethylation at specific sites or in specific regions in a number of genes is correlated with active transcription. Doerfler, W., *Annu. Rev. Biochem.* 52:93–124 (1984); Christman, J. K., *Curr. Top. Microbiol. Immunol.* 108:49–78 (1988); Cedar, H., *Cell* 34:5503–5513 (1988). DNA methylation in vitro can prevent efficient transcription of genes in a cell-free system or transient expression of transfected genes. Methylation of C residues in some specific cis-regulatory regions can also block or enhance binding of transcriptional factors or repressors. Doerfler, W., *Annu. Rev. Biochem.* 52:93–124 (1984); Christman, J. K., *Curr. Top. Microbiol. Immunol.* 108:49–78 (1988); Cedar, H., *Cell* 34:5503–5513 (1988); Tate, P. H. et al., *Curr. Opin. Genet. Dev.* 3:225–231 (1993); Christman, J. K. et al., Virus Strategies, eds. Doerfler, W. & Bohm, P. (VCH, Weinheim, N.Y.) pp. 319–333 (1993).

Disruption of normal patterns of DNA methylation has been linked to the development of cancer. Christman, J. K. et al., *Proc. Natl. Acad. Sci. USA* 92:7347–7351 (1995). The 5-MeC content of DNA from tumors and tumor derived cell lines is generally lower than normal tissues. Jones, P. A. et al., *Adv. Cancer Res* 40:1–30 (1983). Hypomethylation of specific oncogenes such as c-myc, c-Ki-ras and c-Ha-ras has been detected in a variety of human and animal tumors. Nambu, S. et al., *Jpn. J. Cancer (Gann)* 78:696–704 (1987); Feinberg, A. et al., *Biochem. Biophys. Res. Commun.* 111:47–54 (1983); Cheah, M. S. C. et al., JNCI 73:1057–1063 (1984); Bhave, B. R. et al., *Carcinogenesis (Lond)* 9:343–348 (1988). In one of the best studied examples of human tumor progression, it has been shown that hypomethylation of DNA is an early event in development of colon cancer. Goetz, S. E. et al., *Science* 228:187–290 (1985). Interference with methylation in vivo can lead to tumor formation. Feeding of methylation inhibitors such as L-methionine or 5-azacytodine or severe deficiency of 5-adenosine methionine through feeding of a diet depleted of lipotropes has been reported to induce formation of liver tumors in rats. Wainfan, E. et al., *Cancer Res.* 52:2071s–2077s (1992). Studies show that extreme lipotrope deficient diets can cause loss of methyl groups at specific sites in genes such as c-myc, ras and c-fos. Dizik, M. et al., *Carcinogenesis* 12:1307–1312 (1991). Hypomethylation occurs despite the presence of elevated levels of DNA MTase activity. Wainfan, E. et al., *Cancer Res.* 49:4094–4097 (1989). Genes required for sustained active proliferation become inactive as methylated during differentiation and tissue specific genes become hypomethylated and are active. Hypomethylation can then shift the balance between the two states. The present invention thus takes advantage of this naturally occurring phenomena, to provide compositions and methods for site specific methylation of specific gene promoters, thereby preventing transcription and hence translation of certain genes.

Since the c-Ha-ras oncogene is known to be involved in the development of human breast cancer, the MCF-7 cell line was used to evaluate the effect of RZ1X on cell proliferation in vitro. The MCF-7 cell line has been studied extensively and is known to respond to compounds that inhibit ras protein function. RZ1X was delivered without using any enhancer to facilitate delivery. A single 10 μM treatment was able to inhibit cell growth 80 to 90% and the inhibitory effect was sustained for several weeks without further treatment. Other similarly modified synthetic oligonucleotides with a random sequence or those complement to the other regions of the ras oncogene, as well as other genes not involved in the development of breast cancer, showed no effects. RZ1X was also effective in inhibiting cell proliferation and tumorigenicity of the breast tumor cell line, MDA-MB 435, while it had no effect on other cells including MCF10A, a normal human breast cell line. Northern blotting of the total RNA shows that c-Ha-ras oncogene has been down regulated by the RZ1X oligonucleotide.

Any of the known methods of oligonucleotide synthesis can be used to prepare the modified oligonucleotides of the present invention wherein the nucleotide, dC is replaced by 5-methyl-dC where appropriate, as taught by the present invention. The modified oligonucleotides are most conveniently prepared by using any of the commercially available automated nucleic acid synthesizers. They can also be obtained from commercial sources which synthesize custom oligonucleotides pursuant to customer specifications.

Although the c-Ha-ras oncogene promoter was used to make RZ1X, it will be appreciated that any gene promoter may be used as a template to make a methylated antisense oligonucleotide to inhibit transcription of any undesired gene, e.g., c-Ki-ras and c-N-ras. For example, the oligonucleotides of the present invention may be used in the treatment of cancers, infectious diseases and autoimmune diseases. In the treatment of cancers, the target sequences can be DNA or RNA associated with oncogenes such as c-raf and c-myc, tumor suppressor genes, genes associated with multiple drug resistance (i.e., gene for P-glycoprotein) and other related genes. In the treatment of infectious diseases, the target sequences include those genes associated with AIDS, Herpes, drug resistant plasmids, and Trypanosomes. For the treatment of autoimmune diseases, the modified oligonucleotides may be target sequences associated with Rheumatoid arthritis, Type I diabetes, systemic lupus and multiple sclerosis.

The modified oligonucleotides of the present invention may be administered for therapeutic treatment in any suitable manner, preferably with pharmaceutically acceptable carriers. One skilled in the art will appreciate that suitable methods of administering such compounds are available. Pharmaceutically acceptable carries are also well known to those skilled in the art. The choice of carrier will be determined in part by the particular modified oligonucleotide, as well as by the particular method used to administer the composition. In practicing the present invention, the modified nucleotide can be administered, for example, by intravenous infusion, orally, topically, intraperitoneally, intrevesically or intrathecally.

The following Specific Examples illustrate practice of the invention. These examples are for illustrative purposes only and are not intended in any way to limit the scope of the claimed invention.

SPECIFIC EXAMPLE 1

A 26-mer oligonucleotide (RZ1X; SEQ ID NO: 1) was synthesized with 5-MeC in each of its six CpG sites. RZ1X is complementary to the sense strand DNA of a specific region of c-Ha-ras promoter, located upstream of TATA box, between bases 485 and 511. The sequence of RZ1X is: 5'-GGCGCGCGGTTCGCCCCGCGCATGGG-3' (SEQ ID NO: 1) where C represents 5-MeC.

A second oligo was synthesized (RZ4X; SEQ ID NO: 3) complementary to a region between 1641 and 1673, 31 bases long upstream but close to TATA box. The rational for selecting RZ1X was its rich CpG sites. RZ4X was selected because of its proximity to TATA box where some transcriptional factors might bind to trigger a transcriptase enzyme. Since human breast cancers are known to respond to compounds that inhibit Ras protein function, the MCF-7 cell line was used to evaluate the effect of RZ1X and RZ4X on cell proliferation in vitro. The MCF-7 cell line has been studied extensively and is known to have a mutated ras oncogene. A one time addition of RZ1X to MCF-7 cell culture without any enhancer to facilitate delivery, resulted in greater than 90% inhibition of cell growth (Table 1). The slow growth was sustained without further addition of RZ1X. RZ4X on the other hand showed no effect under the same conditions. Unmethylated oligonucleotides (RZ1; SEQ ID NO: 2) were less effective compared to those methylated, and a significant difference was observed in the second week of their effect. Slow growth rate was maintained when cells were examined two weeks after a single treatment with RZ1X while the inhibition was reversed for those treated with RZ1. Whether the selected sites of the promoter region were methylated or the inhibition is due to RZ1X interference with transcription, remains unclear.

To establish sequence specificity of RZ1X, two other methylated oligonucleotides, one complementary to a similar region of 12-lipoxygenase enzyme (RH1X; SEQ ID NO: 4), and a second modified oligonucleotide that has the same sequence as RZ1X but scrambled (RMX; SEQ ID NO: 5), were used to treat MCF-7. These had no effect on cell growth (Table 1).

Figure 2:
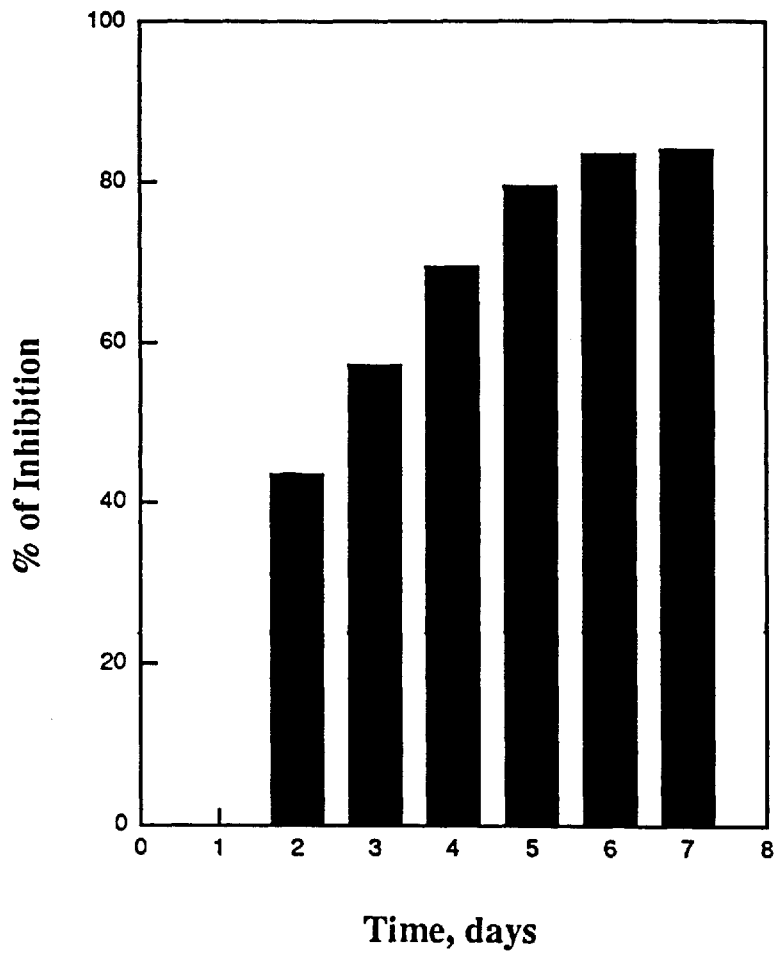
FIG. 2 is a graph showing MCF-7 cell growth inhibition, using specific modified anti-ras oligonucleotides.

Dose response data (FIG. 1), shows that inhibition of cell growth was in fact due to the presence of oligonucleotides. The lowest concentration of oligonucleotides which gives a near maximum effect is 10 µM. The result of the time coarse experiment (FIG. 2) indicates that the mechanism of RZ1X effect on cell growth is different from that of conventional antisense oligonucleotides which interferes with ribosomal translation. The effect of RZ1X becomes visible two days after treatment and increases every day until it is maximized around day 6 while antisense drugs generally act within a few hours and last 20 min.

TABLE 1

Effect of oligonucleotides on MCF-7 cell growth

| | # of MCF-7 Cells | | |
|---|---|---|---|
| Oligonucleotides | Day 0 | Day 7 | % Inhibition |
| Control | $2 \times 10^5$ | $3.30 \times 10^6$ | 0 |
| RZ1X[1] | $2 \times 10^5$ | $0.38 \times 10^6$ | 88.5 |
| RZ1[2] | $2 \times 10^5$ | $1.10 \times 10^6$ | 66.5[a] |
| RZ4X[3] | $2 \times 10^5$ | $3.40 \times 10^6$ | 0 |
| RH1X[4] | $2 \times 10^5$ | $3.30 \times 10^6$ | 0 |
| RMX[5] | $2 \times 10^5$ | $3.35 \times 10^6$ | 0 |

[1]RZ1X, a modified anti-ras oligonucleotide. (SEQ ID NO: 1)
[2]RZ1, unmodified anti-ras oligonucieotide. (SEQ ID NO: 2)
[3]RZ4X, a modified anti-ras oligo of a different region. (SEQ ID NO: 3)
[4]RH1X, a modified anti-12 lipoxygenase oligonucleotide. (SEQ ID NO: 4)
[5]RMX, a modified oligonucleotide with a random sequence. (SEQ ID NO: 5)
[a]MCF-7 cells treated with RZ1 and RZ1X were incubated for an additional week in fresh media in the absence of oligonucleotides. RZ1-treated cells fully recovered, while the inhibitory effect of RZ1X was preserved.

Materials and Methods

Synthesis and purification of oligonucleotides. Phosphoramidites of dC, dG, dA, dT and 5-methyl-dC (Pharmacia) were used to synthesize oligonucleotides, using a Pharmacia Gene Assembler automated oligonucleotide synthesizer. The protocol for the synthesis of oligonucleotides is in the Pharmacia users manual. The oligonucleotides were cleaved from the support column with concentrated NH$_4$OH, deprotected at 55° C. for 18 h and purified by HPLC using Aquapore RP-300 (C8) column and eluted with a 4–80% acetonitrile gradient in 50 mM triethylamine acetate. The alternative method for purification of oligonucleotides is gel electrophoresis. Oligonucleotides are loaded on 1% agarose gel and corresponding bands are cut and electro eluted in 1× TBE buffer. Oligonucleotides are extracted with phenol:chloroform (1:1) and precipitated using ethanol sodium acetate. They are dried under vacuum and dissolved in sterile 1× PBS or H$_2$O. The oligonucleotides can also be commercially synthesized, wherein the method of synthesis is similar to the above protocol.

Cell culture. Human breast tumor cell line, MCF-7 was established in 1973. Nambu, S. et al., *Jpn. J. Cancer* (Gann) 78:696–704 (1987). The cells were obtained from Karmanos Cancer Institute and are also commercially available. Aliquots of MCF-7 cells at 170° C. were also frozen. Cells were cultured in minimum essential medium (MEM; Gibco Life Technologies) supplemented with 5% fetal calf serum and antibiotics (complete MEM). Cultures were maintained in a 5% CO$_2$ incubator. Growth of the cultures was monitored by allowing the cells to swell in hypotonic HEPES buffer (0.01 M HEPES, 0.001 5M MgCl$_2$), after which the cells were lysed with detergent (0.13 Methylhexadecyldimethyl- ammonium bromide, 3% vol/vol glacial acetic acid) and the number of nuclei in the resulting suspension were determined utilizing a Coulter Counter. Alternatively the cells can be detached from flasks using 1% Trypsin, washed with 1× PBS and resuspended in complete MEM. The cells were then counted using trypan blue dye exclusion assay (0.1% trypan blue) and hemacytometer. This technique allows the determination of the number of both dead and live cells in both control and experimental cultures.

Oligonucleotide treatment. All modified, unmodified and control oligonucleotides were tested on MCF-7 cells, clone E3, passage number 182. Cells were seeded in T-25 flasks (Corning Science Products, Corning N.Y.) at 2.0×10$^5$ cells per flask in 3 ml of complete MEM. One day after passage, the media was replaced with 3 ml of fresh complete MEM and oligonucleotides were added to a final concentration of 20 µM. There were 6 flasks for each compound, 3 control and 3 experimental flasks. The media was replaced every 48 h without further addition of oligonucleotides. The cells were harvested on day 7 when control cultures were confluent, and counted as described. The percentage of inhibition was then calculated.

SPECIFIC EXAMPLE 2

To show that the inhibitory effect of RZ1X was not simply a general toxic effect on any cell line and to further examine sequence specificity, the MCF10A cell line, which is a normal human breast cell line, along with colon carcinoma cells (Clone A), prostatic carcinoma cells (DU145) and friend erythroleukemia cells (FLC) were studied. RZ1X had an approximate 15% inhibitory effect on cell proliferation of DU145 and no effect on the other cell lines (Table 2). The 15% inhibitory effect on DU145 may be due to sequence homology between c-Ha-ras and c-Ki-ras, an oncogene known to be involved in the development of prostate cancer.

TABLE 2

Effect of Specific Anti-Ras Oligonucleotides on Different Cell Lines

| Cell Lines | # of Cells | | % Inhibition |
|---|---|---|---|
| | Day 0 | Day 7 | |
| MCF-7 | C 2 × 10$^5$ | 4.6 × 10$^6$ | |
| | T 2 × 10$^5$ | 0.8 × 10$^6$ | 82.6 |
| MCF10A | C 2 × 10$^5$ | 2.0 × 10$^6$ | |
| | T 2 × 10$^5$ | 2.0 × 10$^6$ | 0 |
| Clone A | C 2 × 10$^5$ | 2.5 × 10$^6$ | |
| | T 2 × 10$^5$ | 3.0 × 10$^6$ | 0 |
| DU145 | C 2 × 10$^5$ | 1.9 × 10$^6$ | |
| | T 2 × 10$^5$ | 1.6 × 10$^6$ | 15 |

TABLE 2-continued

Effect of Specific Anti-Ras Oligonucleotides on Different Cell Lines

| Cell Lines | # of Cells | | % Inhibition |
|---|---|---|---|
| | Day 0 | Day 7 | |
| FLC | C 2 × 10$^5$ | 4.6 × 10$^6$ | |
| | T 2 × 10$^5$ | 4.5 × 10$^6$ | 0 |

C = control
T = treated cells

Materials and Methods

MCF-7, MCF-10A, Clone A, DU145, and FLC, were all treated with RZ1X (10 µM). The cells were treated only once and the media was changed every 48 hours. All cells were counted 7 days after treatment except for FLC which were counted after 48 hrs.

SPECIFIC EXAMPLE 3

Figure 3:
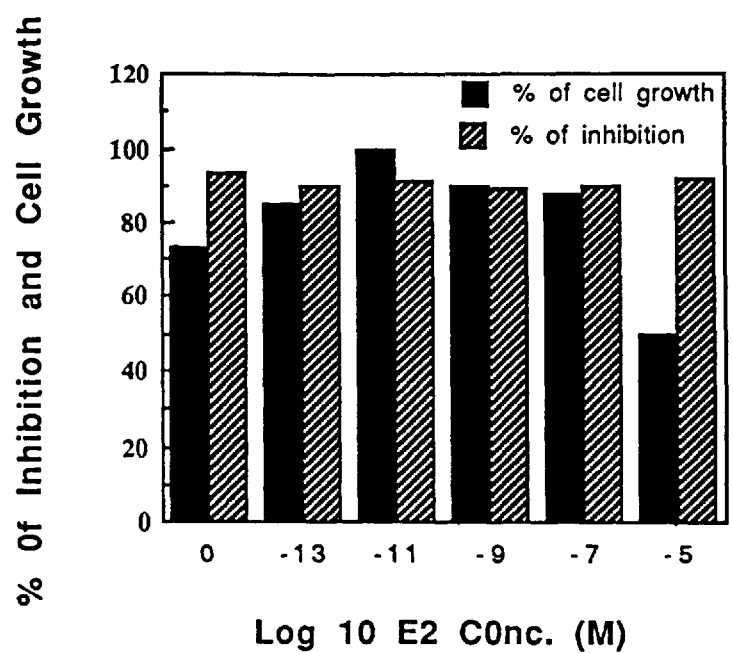
FIG. 3 is a graph showing the effect of anti-ras oligonucleotides on MCF-7 cell growth in the presence of estrogen.
Figure 4:
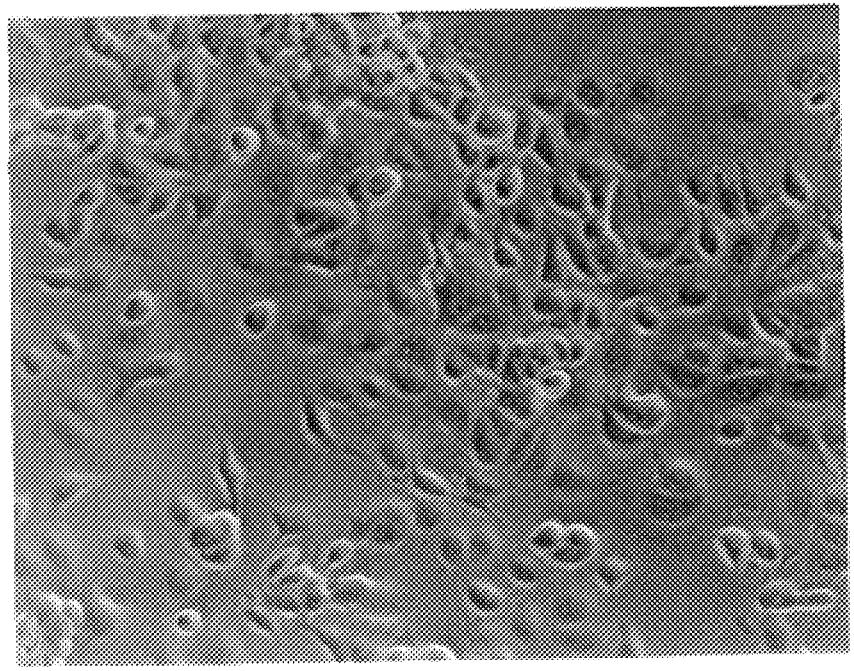
FIG. 4 is a photograph (×400) of MCF-7, clone E3, after 7 days growth in media containing $10^{-11}$ estrogen.
Figure 5:
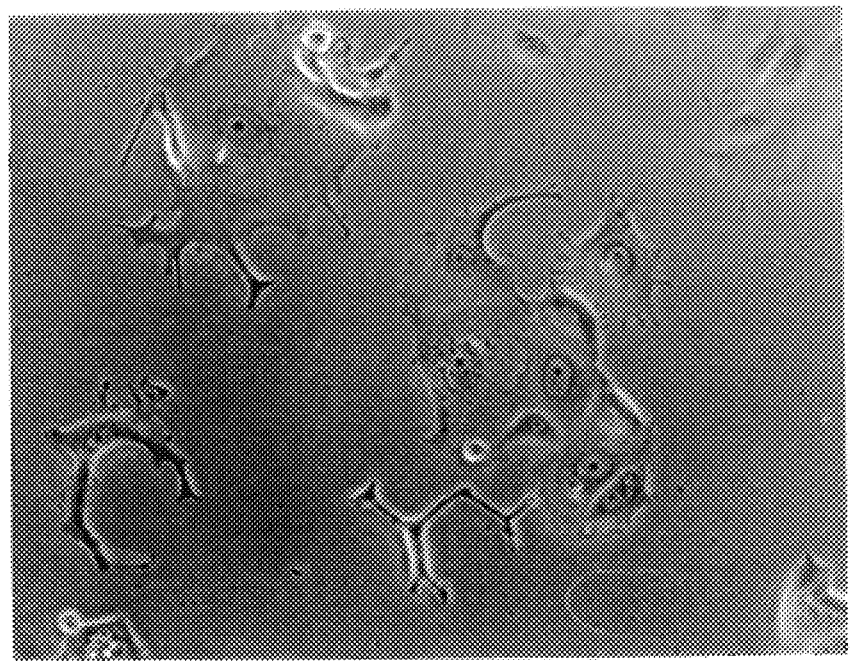
FIG. 5 is a photograph (×400) of MCF-7, clone E3, seven days after one treatment with 20 μM anti-ras oligos.
Figure 5:
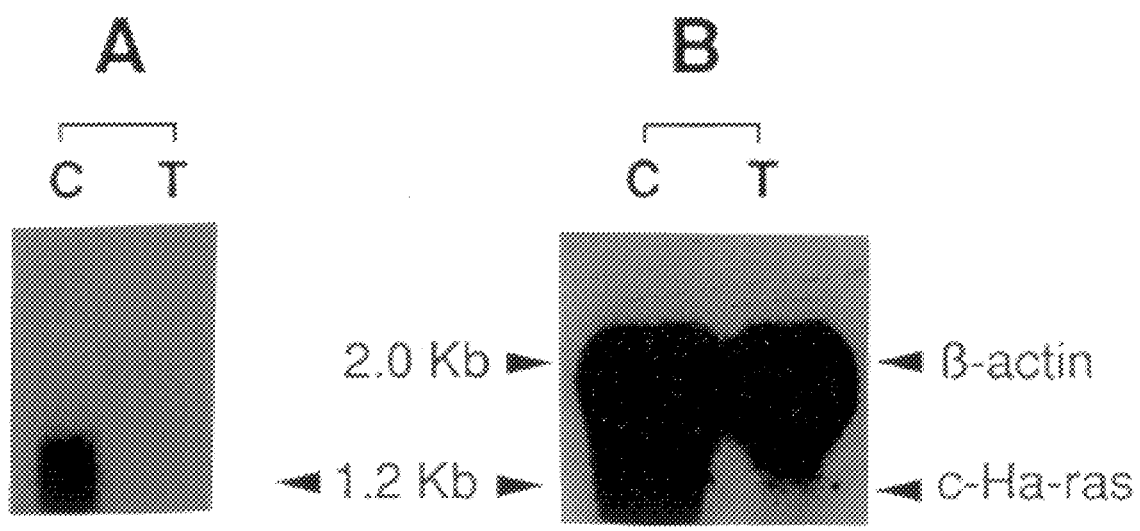

Since the media used for MCF-7 cell culture contained estrogen (E3), a study was performed to determine whether estrogen played any role in inhibition of cell growth. The effect of RZ1X oligo in the presence of various concentrations of E3 was examined. MCF-7 cells were seeded in T-25 flasks overnight. The media was then replaced with fresh media containing various concentration of E3 and cells were treated with 10µM anti-ras oligonucleotides. The cells were counted on day 7 when the control flasks were confluent. Although cell growth was varied at different concentrations of E3 (FIG. 3), the percentage of inhibition was independent of E3 concentration. The cell shape and size when examined under light microscope also indicated their slow growth (FIGS. 4 and 5). The cells are smaller when they divide rapidly while treated cells are bigger in size and spread more. Cell mortality appeared to be the same for both control and treated cells (normally around 5–10% depending on media freshness and cell concentration in culture).

SPECIFIC EXAMPLE 4

Northern blotting of total RNA extracted from both control and treated cell was used to establish that inhibition of MCF-7 cell growth was due to down regulation of the ras oncogene. Data shows that inhibition of gene expression is at the transcriptional level and may explain why RZ1X has a much longer inhibitory effect than conventional antisense oligonucleotides (FIG. 6). In FIG. 6, C represents control RNA from untreated cells and T represents RNA from cells treated with 20 µM anti-ras oligonucleotides.

Materials and Methods

RNA isolation. There are many methods for isolating RNA and are all reliable as long as cautionary effort is taken to keep RNA from contamination and degradation. Tri-Reagent (MRC, Inc.) was successfully used to isolate RNA from many cell lines. Cells grown in monolayer were directly lysed (1 ml Tri-Reagent per 5–10×10$^6$ cells) by passing several times through a pipette. Homogenized sample was stored at room temperature for 5 min. It was then extracted with 0.2 ml of chloroform. RNA remained in the upper aqueous phase and was precipitated with 0.5 ml isopropanol. Pellet was washed with 75% ethanol, air-dried and dissolved in DEPC-treated H$_2$O. RNA solution was incubated 10–15 min at 55°–60° C. and concentration was measured. Northern blotting of total RNA. 30 mg of the total RNA extracted from both control and treated MCF-7 cells were electrophoresed on 1% formaldehyde-agarose gel and transferred to Gene Screen nitrocellulose membrane. The membrane was then prehybridized at 42° C. with solution containing 50% formamide, 0.5% dextran sulfate, 5× Denhardt's, 0.05M sodium phosphate, 5× SSC and 300 mg/ml denatured salmon sperm DNA. Hybridization was carried in the same solution, containing randomly primed $^{32}$P-labeled c-Ha-ras cDNA probe (500 bp) (labeling kit, Pharmacia) at 42° C. overnight. The membrane was washed at 55° C. with 2× SSC, 0.1% SDS for 30–60 min. It was further washed in 0.2× SSC, 0.1% SDS 30 min and 0.1% SDS for 15 min. The membrane was then autoradiographed. The same membrane was hybridized with β-actin cDNA probe to show that the quantity of RNA from control and treated cells was the same.

SPECIFIC EXAMPLE 5

Figure 7A:
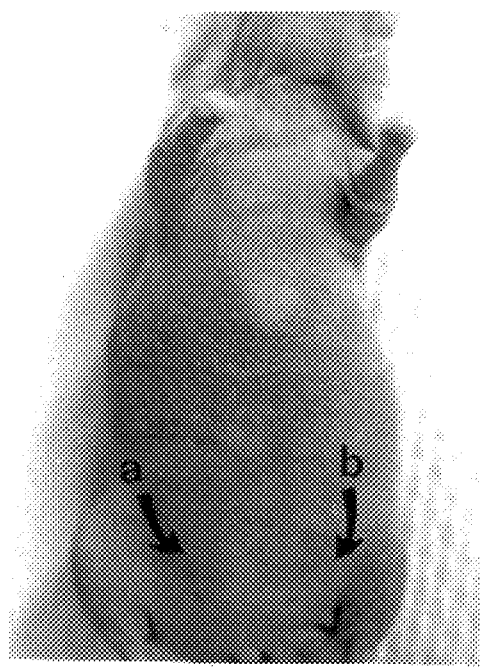
FIG. 7A is a photograph of a nude mouse taken two months after being injected with $1\times10^5$ MDA-MB 435 (human breast tumor cell line) cells which have been treated with 20 μM RZ1X (anti-ras oligonucleotide)
Figure 7B:
FIG. 7B is a photograph of the control animal injected with tumorigenic MDA-MB 435 cells, treated with scrambled RZ1X, which had no inhibitory effect on cell growth.

An in vivo experiment was performed to determine whether RZ1X has any effect on cell tumorigenicity. A tumorigenic human breast cell line, MDA-MB 435, and nude mice were used. $1\times10^5$ cells were sufficient to develop a tumor in one site two weeks after injection. Inhibition of MDA-MB435 cell growth was identical to that of MCF-7 cells in situ. Two weeks after injection of both control and treated cells into mammary fat pads of nude mice, tumors of 2–4 mm were detected in all 4 control mice but not treated mice. Two months after injection, 4 control mice had tumors 10 to 24 mm in size (Table 3) and 3 out of 4 treated mice had no tumor at all (FIG. 7A, wherein a and b are the sites of injection). The one animal which appeared to have a tumor was further examined and it was indicated to be due to infection. There was no sign of metastasis. Tumors in control mice were metastasized in most internal organs such as lymph nodes, liver and spleen (FIG. 7B, wherein c locates the location of the tumor).

TABLE 3

Inhibition Of Tumorigenicity In Nude Mice

| | 1 | 2 | 3 | 4 |
|---|---|---|---|---|
| Control | 24 × 18* | 22 × 25 | 22 × 14 | 12 × 10 mm |
| Treated | 0 | 0 | 0 | 6 × 6** mm |

*Tumor was metastasized in most internal organs such as lymph nodes, liver and spleen.
**80% of the tumor size was due to infection.

Materials and Methods

In vivo studies. MDA-MB 435 cells were treated once with 20 μM RZ1X for 4 days. Control cells were simultaneously treated with a scrambled oligo, having the same base composition as RZ1X. Control and RZ1X treated MDA-MB435 cells were injected ($1\times10^5$ cell/site) into the right mammary fat pad region of 8 week old Ncr nu/nu mice (NCI, Frederick, Md.). They were checked once a week for the development of tumor. When the tumors reached a size larger than 1.5 cm and showed signs of necrosis, tumors were measured and tumor-bearing mice were euthanized and dissected to examine the tumors and their metastatic states.

SPECIFIC EXAMPLE 6

Treatment of certain diseases such as cancer can be achieved by administration of the methylated antisense oligonucleotides of the present invention that specifically inhibit the expression of the oncogene unique to that cancer. In one embodiment of the invention, a method for treating cancer characterized by mutations in the ras gene is provided. Such cancers include without limitation, those of the bladder, breast, colon, lung, ovary, pancreas, prostate and thyroid. A methylated oligonucleotide effective against the type of cancer with which a patient is afflicted is administered to the patient. Those skilled in the medical oncology arts will readily appreciate that the doses and schedules of the oligonucleotide delivery will vary depending on the age, health, sex, size and weight of the patient, the route of administration, and the relative susceptibilities of the cancer to the oligonucleotide. These parameters may be determined by well-established procedures and analysis.

For example, the oligonucleotide of SEQ ID NO: 1 may be administered to patients intravenously at 0.5–5 mg/kg body weight on a daily dosing regime. For such administration the oligonucleotides can be combined with a pharmaceutically acceptable carrier, such as a suitable liquid vehicle or excipient and an optional auxiliary additive or additives. The liquid vehicles and excipients are conventional and commercially available. Illustrative thereof are distilled water, physiological saline, aqueous solutions of dextrose and the like.

The pharmaceutical preparations of the present invention are manufactured in a manner which is itself well known in the art. For example, the pharmaceutical preparations may be made by means of conventional mixing, granulating, dragee-making, dissolving, or lyophilizing processes.

Pharmaceutical preparations which may be used orally include push-fit capsules made of gelatin, as well as soft, sealed capsules made of gelatin and a plasticizer such as glycerol or sorbitol. The push-fit capsules can contain the active compounds (i.e., oligonucleotides) in the form of granules which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, liquid paraffin, or liquid polyethylene glycols. In addition, stabilizers may be added.

Pharmaceutical preparations which can be used rectally include, for example, suppositories, which consist of a combination of the active compounds with a suppository base. Suitable suppository bases are, for example, natural or synthetic triglycerides, paraffin hydrocarbons, polyethylene glycols, or high alkanols. In addition, it is also possible to use gelatin rectal capsules which consist of a combination of the active compounds with a base. Possible base material include, for example, liquid triglycerides, polyethylene glycols, or paraffin hydrocarbons.

Pharmaceutical preparations for parenteral administration include aqueous solutions of the active compounds in water-soluble or water-dispersible form. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances which increase the viscosity of the suspension include, for example, sodium carboxymethyl cellulose, sorbitol, and/or dextran, optionally, the suspension may also contain stabilizers.

In addition to administration with conventional carriers, the active compounds may be administered by a variety of specialized delivery techniques. For example, the compositions of the present invention may also be administered encapsulated in liposomes, pharmaceutical compositions wherein the active ingredient is contained either dispersed or variously present in corpuscles consisting of aqueous concentric layers adherent to lipidic layers. The active compounds, depending upon solubility, may be present both in the aqueous layer and in the lipidic layer, or in what is generally termed a liposomic suspension. The hydrophobic layer, generally but not exclusively, comprises phopholipids such as lecithin and sphingomyelin, steroids such as cholesterol, more or less ionic surfactants such as diacetylphosphate, stearylamine, or phosphatidic acid, and/ or other materials of a hydrophobic nature. The diameters of the liposomes generally range from about 15 nm to about 5 microns.

The foregoing discussion discloses and describes merely exemplary embodiments of the present invention. One skilled in the art will readily recognize from such discussion, and from the accompanying drawings and claims, that various changes, modifications and variations can be made therein without departing from the spirit and scope of the invention as defined in the following claims.

All patents and other publications cited herein are expressly incorporated by reference.

We claim:

1. An oligonucleotide having the sequence of SEQ ID NO: 1, wherein all cytosine bases in CG dinucleotide pairs are 5-methylcytosine.

2. A method of inhibiting the expression of the c-Ha-ras gene in a cell, comprising the step of administering to the cell the oligonucleotide of claim 1.

3. A method of inhibiting the expression of the c-Ki-ras gene in a cell, comprising the step of administering to the cell the oligonucleotide of claim 1.

4. A method of inhibiting the expression of the c-N-ras gene in a cell, comprising the step of administering to the cell the oligonucleotide of claim 1.

5. A method of inhibiting transcription of the c-Ha-ras gene in a cancer cell comprising the step of administering to the cell the oligonucleotide of claim 1.

6. A composition comprising a pharmaceutically acceptable carrier and the oligonucleotides of claim 1.

7. An oligonucleotide having the sequence of SEQ ID NO: 1, wherein at least one of the cytosine bases in a CG dinucleotide pair is 5-methylcytosine.

8. A composition comprising a pharmaceutically acceptable carrier and the oligonucleotides of claim 7.

9. A method of inhibiting the expression of the c-Ha-ras gene in a cell, comprising the step of administering to the cell the oligonucleotide of claim 7.

10. A method of inhibiting the expression of the c-Ki-ras gene in a cell, comprising the step of administering to the cell the oligonucleotide of claim 7.

11. A method of inhibiting the expression of the c-N-ras gene in a cell, comprising the step of administering to the cell the oligonucleotide of claim 7.

12. A method of inhibiting transcription of the c-Ha-ras gene in a cancer cell comprising the step of administering to the cell the oligonucleotide of claim 7.

* * * * *

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: Not Relevant ( i i ) MOLECULE TYPE: other nucleic acid
        ( A ) DESCRIPTION: /desc = "Nucleic acid probes"

( i i i ) HYPOTHETICAL: YES ( i v ) ANTI-SENSE: YES ( i x ) FEATURE:
        ( A ) NAME/KEY: modified_base
        ( B ) LOCATION: one-of(3, 5, 7, 12, 17, 19)..19
        ( C ) IDENTIFICATION METHOD: experimental
        ( D ) OTHER INFORMATION: /evidence=EXPERIMENTAL
            / frequency= 0.99
            / mod_base= m5c
            / note="All cytidine (C) bases of CG sites are fully methylated"

( x i ) SEQUENCE DESCRIPTION: SEQ ID NO:1:

GGCGCGCGGT TCGCCCCGCG CATGGG        26

( 2 ) INFORMATION FOR SEQ ID NO:2:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: Not Relevant ( i i ) MOLECULE TYPE: other nucleic acid
        ( A ) DESCRIPTION: /desc = "Nucleic acid probes"

( i i i ) HYPOTHETICAL: YES ( i v ) ANTI-SENSE: YES ( x i ) SEQUENCE DESCRIPTION: SEQ ID NO:2:

GGCGCGCGGT TCGCCCCGCG CATGGG        26

( 2 ) INFORMATION FOR SEQ ID NO:3:

( i ) SEQUENCE CHARACTERISTICS:
        ( A ) LENGTH: 31 base pairs
        ( B ) TYPE: nucleic acid
        ( C ) STRANDEDNESS: single (D) TOPOLOGY: Not Relevant (i i) MOLECULE TYPE: other nucleic acid
    (A) DESCRIPTION: /desc = "Nucleic acid probe"

(i v) ANTI-SENSE: YES (i x) FEATURE:
    (A) NAME/KEY: modified_base
    (B) LOCATION: one-of(4, 10, 26)..one- of(4, 10, 26)
    (C) IDENTIFICATION METHOD: experimental
    (D) OTHER INFORMATION: /evidence=EXPERIMENTAL
        / frequency= 0.99
        / mod_base= m5c
        / note= "All cytidine (C) bases in CG sites are fully methylated"

(x i) SEQUENCE DESCRIPTION: SEQ ID NO:3:

TTCCGTCATC GCTCCTCAGG GCCTGCGGCC C 31

(2) INFORMATION FOR SEQ ID NO:4:

(i) SEQUENCE CHARACTERISTICS:
    (A) LENGTH: 29 base pairs
    (B) TYPE: nucleic acid
    (C) STRANDEDNESS: single
    (D) TOPOLOGY: Not Relevant (i i) MOLECULE TYPE: other nucleic acid
    (A) DESCRIPTION: /desc = "Nucleic acid probe"

(i v) ANTI-SENSE: YES (i x) FEATURE:
    (A) NAME/KEY: modified_base
    (B) LOCATION: one-of(3, 10, 16, 25)..one-of(3, 10, 16, 25)
    (C) IDENTIFICATION METHOD: experimental
    (D) OTHER INFORMATION: /evidence=EXPERIMENTAL
        / frequency= 0.99
        / mod_base= m5c
        / note= "All cytidine (C) bases in CG sites are fully methylated"

(x i) SEQUENCE DESCRIPTION: SEQ ID NO:4:

ACCGGTCTGC GGCCCCGCCC TCCTCGCAA 29

(2) INFORMATION FOR SEQ ID NO:5:

(i) SEQUENCE CHARACTERISTICS:
    (A) LENGTH: 26 base pairs
    (B) TYPE: nucleic acid
    (C) STRANDEDNESS: single
    (D) TOPOLOGY: Not Relevant (i i) MOLECULE TYPE: other nucleic acid
    (A) DESCRIPTION: /desc = "Nucleic acid probe"

(i v) ANTI-SENSE: YES (i x) FEATURE:
    (A) NAME/KEY: modified_base
    (B) LOCATION: one-of(4, 8, 15)..one- of(4, 8, 15)
    (C) IDENTIFICATION METHOD: experimental
    (D) OTHER INFORMATION: /evidence=EXPERIMENTAL
        / frequency= 0.99
        / mod_base= m5c
        / note= "All cytidine (C) bases in CG site are fully methylated"

(x i) SEQUENCE DESCRIPTION: SEQ ID NO:5:

TGCCGGGCGG TGCCCGGAGG GCCTCC 26